United States Patent
Schroeder

(10) Patent No.: US 7,300,555 B2
(45) Date of Patent: Nov. 27, 2007

(54) METHOD FOR THE RECTIFYING SEPARATION OF LIQUIDS CONTAINING (METH)ACRYLIC MONOMERS IN A RECTIFICATION COLUMN

(75) Inventor: Juergen Schroeder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 192 days.

(21) Appl. No.: 10/531,275

(22) PCT Filed: Nov. 17, 2003

(86) PCT No.: PCT/EP03/12815

§ 371 (c)(1),
(2), (4) Date: Apr. 13, 2005

(87) PCT Pub. No.: WO2004/050596

PCT Pub. Date: Jun. 17, 2004

(65) Prior Publication Data

US 2006/0151309 A1 Jul. 13, 2006

(30) Foreign Application Priority Data

Nov. 29, 2002 (DE) ................ 102 56 147

(51) Int. Cl.
- *B01D 3/42* (2006.01)
- *C07C 57/07* (2006.01)
- *C07C 57/075* (2006.01)
- *C07C 69/533* (2006.01)

(52) U.S. Cl. ............. 203/1; 203/3; 203/49; 203/98; 203/DIG. 21; 560/218; 560/205; 562/532; 562/600

(58) Field of Classification Search ............. 203/1, 203/3, 8, 49, 98, DIG. 21; 560/205, 218; 562/532, 600

See application file for complete search history.

(56) References Cited

U.S. PATENT DOCUMENTS

| 4,260,821 A | 4/1981 | Benjamin |
| 6,423,875 B1 * | 7/2002 | Machhammer et al. ..... 568/476 |
| 6,472,554 B1 * | 10/2002 | Deckert et al. ............. 560/205 |
| 6,939,991 B2 * | 9/2005 | Thiel et al. ................. 562/545 |
| 2001/0007043 A1 | 7/2001 | Machhammer et al. |
| 2004/0116736 A1 | 6/2004 | Machhammer et al. |
| 2004/0249198 A1 | 12/2004 | Thiel et al. |

FOREIGN PATENT DOCUMENTS

| DE | 195 01 325 | 7/1996 |
| DE | 196 06 877 | 8/1997 |
| DE | 199 24 532 | 11/2000 |
| DE | 101 15 277 | 6/2002 |
| DE | 101 56 988 | 5/2003 |
| DE | 102 18 419 | 6/2003 |
| DE | 102 24 341 | 7/2003 |
| DE | 102 38 145 | 11/2003 |
| EP | 0 717 029 | 6/1996 |
| EP | 0 982 287 | 3/2000 |
| EP | 0 982 289 | 3/2000 |
| EP | 1 029 573 | 8/2000 |
| EP | 1 046 416 | 10/2000 |
| EP | 1 125 912 | 8/2001 |

OTHER PUBLICATIONS

Stefanie Schulze and Herbert Vogel: "Aspects of the Safe Storage of Acrylic Monomers: Kinetics of the Oxygen Consumption" Chem.Eng.Technol., vol. 21, No. 10, pp. 829 to 836, 1998.

* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for rectificatively separating liquids containing (meth)acrylic monomers in a rectification column is provided, in which a stream is withdrawn from the rectification column and recycled into the rectification column as a molecular oxygen-enriched liquid phase.

7 Claims, No Drawings

METHOD FOR THE RECTIFYING SEPARATION OF LIQUIDS CONTAINING (METH)ACRYLIC MONOMERS IN A RECTIFICATION COLUMN

The present invention relates to a process for rectificatively separating liquids comprising (meth)acrylic monomers in a rectification column by withdrawing a stream from the rectification column at at least one withdrawal point during rectification, treating the stream withdrawn and, after the treatment, recycling at least a portion of this stream as a liquid phase into the rectification column at at least one recycle point.

In this document, the term (meth)acrylic monomers is an abbreviation for "acrylic monomers and/or methacrylic monomers".

In this document, the term acrylic monomers is an abbreviation for "acrolein, acrylic acid and/or esters of acrylic acid".

In this document, the term methacrylic monomers is an abbreviation for "methacrolein, methacrylic acid and/or esters of methacrylic acid".

In particular, the (meth)acrylic monomers addressed in this document are intended to include the following (meth) acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparing polymers which find use, for example, as adhesives.

(Meth)acrolein and (meth)acrylic acid are prepared on the industrial scale predominantly by catalytic gas phase oxidation of suitable $C_3/C_4$ precursor compounds, in particular of propene and propane in the case of acrolein and acrylic acid, or of isobutene and isobutane in the case of methacrylic acid and of methacrolein. However, suitable starting materials in addition to propene, propane, isobutene and isobutane are other compounds containing 3 or 4 carbon atoms, for example isobutanol, n-propanol or the methyl ether (as a $C_4$ precursor) of isobutanol. (Meth)acrylic acid can also be obtained from (meth)acrolein.

This normally results in a product gas mixture from which the (meth)acrylic acid or the (meth)acrolein has to be removed.

This removal is generally carried out in such a way that the (meth)acrylic acid or the (meth)acrolein is initially separated in a basic manner by absorption into a solvent (for example water or an organic solvent) or by fractional condensation of the product gas mixture, and the resulting condensate or absorbate is subsequently separated rectificatively (generally in more than one stage) to obtain more or less pure (meth)acrylic acid or (meth)acrolein (cf., for example, EP-A 717019, EP-A 1125912, EP-A 982289, EP-A 982287, DE-A 19606877, DE-A 1011527, DE-A 10224341, DE-A 10218419). Instead of fractional condensation, a total condensation can also initially be applied and the resulting condensate subsequently worked up rectificatively.

The fractional condensation addressed above should itself not be regarded in this document as falling under the definition of a rectificative separation of a liquid, because it differs from such rectification in that the mixture to be separated is fed to the separating column not in liquid form but in gaseous form (i.e. completely converted to the vapor form). Otherwise, the desired separating action in a rectification is achieved by the mass transfer between vapor rising in the rectification column and falling reflux liquid.

Esters of (meth)acrylic acid are obtainable, for example, by direct reaction of (meth)acrylic acid and/or (meth)acrolein with the appropriate alcohols. However, liquid product mixtures are generally obtained initially in this case also, from which the (meth)acrylic esters have to be removed, for example rectificatively.

The liquids comprising (meth)acrylic monomers addressed above may comprise the (meth)acrylic monomers either in more or less pure form or in solution.

The solvent may be either aqueous or an organic solvent. The specific type of the solvent is substantially insignificant for the present invention. The content of (meth)acrylic monomers may be $\geq 2$, 5% by weight, or $\geq 10%$ by weight, or $\geq 20%$ by weight, or $\geq 40%$ by weight, or $\geq 60%$ by weight, or $\geq 80%$ by weight, or $\geq 90%$ by weight, or $\geq 95%$ by weight, or $\geq 99%$ by weight.

Depending on their composition, the liquids comprising (meth)acrylic monomers as described may be rectificatively separated in such a way that the (meth)acrylic monomers accumulate at the top of the rectification column, or that the (meth)acrylic monomers accumulate in the bottom of the rectification column. It will be appreciated that the fractions comprising the enriched (meth)acrylic monomers may also be withdrawn in the upper, lower or middle section of the rectification column.

In all cases (in particular those mentioned above), the rectification columns used for the rectificative separation in question may contain at least one sieve tray without runoff segment (cf., for example, DE-A 19924532). However, it will be appreciated that these rectification columns may also contain exclusively sieve trays without runoff segments as the sole separating internals of the rectification column (cf., for example, DE-A 10156988 and EP-A 1029573). It is however also possible to use other separating internals, for example bubble-cap trays and/or structured packings.

Such bubble-cap trays and/or structured packings may also be the sole separating internals in the rectification column.

The rectification may be carried out either under atmospheric pressure or under reduced pressure. Typical bottom temperatures are in the range from 100 to 250° C. and typical top pressures are from 80 to 500 mbar.

Solvents frequently accompanying (meth)acrylic monomers in many cases contain diphyl, for example mixtures of diphenyl ether, diphenyl and o-dimethyl phthalate. An example of a solvent frequently used for the absorption of (meth)acrylic monomers contains approx. 57.4% by weight of diphenyl ether, 20.7% by weight of diphenyl and 20% by weight of o-dimethyl phthalate. Other solvents frequently accompanying (meth)acrylic acid and (meth)acrylic ester are methyl acrylate and ethyl acrylate.

In general, the rectifications in question in this document are effected with polymerization inhibition in the rectification column by means of polymerization inhibitors. These are customarily introduced at the top of the column, but can additionally also be added to the liquid phase and also have already been added to the liquid comprising the (meth) acrylic monomers which is to be separated. Typical representatives of such polymerization inhibitors are phenothiazine, 4-methoxyphenol and 4-hydroxy-2,2,6,6-tetramethylpiperidine N-oxyl. Based on the content of the (meth)acrylic monomers, up to a few hundred ppm by weight of polymerization inhibitors are frequently used.

The aim of polymerization inhibition is to substantially suppress undesired polymer formation as a consequence of undesired polymerization of the (meth)acrylic monomers, since such polymer formation undesirably increases the pressure drop over the rectification column and in extreme cases makes it necessary to interrupt the rectification with washing of the rectification column.

For the purpose of additional polymerization inhibition, it is also known (cf., for example, DE-A 19501325 and Chem. Eng. Technol. 21 (1998) 10, p. 829 to 836) for a molecular oxygen-containing gas to flow through the rectification column during the rectification (cf. also DE-A 10238145).

However, a disadvantage of the prior art processes described is that the overall polymerization-inhibiting action achieved is not completely satisfactory.

A process improvement proposed in DE-A 19501325 is to carry out the rectificative removal of (meth)acrylic acid from a (meth)acrylic acid-containing liquid in such a way, for example, that, at at least one point of the rectifying column, a reflux liquid descending therein is withdrawn from the rectifying column, oligomerized and/or polymerized (meth) acrylic acid present therein is separated and the reflux liquid is subsequently recycled to the rectifying column, although this procedure is also not completely satisfactory under the aspect of polymerization inhibition.

It is an object of the present invention to additionally improve the prior art procedure.

We have found that this object is achieved by a process for rectificatively separating liquids comprising (meth)acrylic monomers in a rectification column by withdrawing a stream from the rectification column at at least one withdrawal point during rectification, treating the stream withdrawn and, after the treatment, recycling at least a portion of this stream into the rectification column as a liquid phase at at least one recycle point, wherein the content $C_R$ in the liquid phase recycled into the rectification column of molecular oxygen, expressed in percent of the weight of this phase, is at least twice as high as the content $C_F$ of molecular oxygen present in the reflux liquid of the rectification column at the recycle point and expressed in percent of the weight of the reflux liquid.

Useful rectification columns for the process according to the invention are all common types. In other words, the rectification column may, for example, be a tray column or a column having random or structured packing. It will be appreciated that the abovementioned internals may also be used in mixed form.

Useful random packings are, for example, rings, helices, saddles, Raschig, Intos or Pall rings, barrel or Intalox saddles, Top-Pak or braids.

Useful separating trays are, for example, bubble-cap trays, sieve trays, valve trays, tunnel-cap trays, Thormann trays and/or dual-flow trays. According to the invention, preference is given to rectification columns whose separating internals are exclusively dual-flow trays (cf., for example, DE-A 10156988, EP-A 1029573 and DE-A 10230219).

The liquids comprising (meth)acrylic monomers to be separated in accordance with the invention may contain the (meth)acrylic monomers either in more or less pure form or in solution. The solvent may be either aqueous or an organic solvent. The specific type of the solvent is substantially insignificant to the invention. The content of (meth)acrylic monomers may be $\geq 2\%$ by weight, or $\geq 5\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

Depending on their composition, the liquids comprising the (meth)acrylic monomers described may be rectificatively separated in accordance with the invention either in such a way that the (meth)acrylic monomers accumulate at the top of the rectification column, or in such a way that the (meth)acrylic monomers accumulate in the bottom of the rectification column. It will be appreciated that the fractions comprising the enriched (meth)acrylic monomers may also be withdrawn in the upper, lower or middle section of the rectification column.

Advantageously, the process according to the invention will be carried out in a rectification column consisting of stripping section and rectifying section.

In other words, the liquid comprising methacrylic monomers to be rectificatively separated is preferably not fed into the bottom but rather at an entry point disposed along the column. The portion of the rectification column disposed below this entry point is referred to as the stripping section and the portion of the rectification column disposed above this entry point as the rectifying section. In this case, the stream to be withdrawn in accordance with the invention at at least one withdrawal point selected in the process according to the invention will advantageously be reflux liquid descending in the rectification column, and said reflux liquid will advantageously be removed from the rectification column above the entry point into it of the liquid comprising (meth)acrylic monomers to be separated in accordance with the invention. The stream treated in accordance with the invention is then advantageously recycled as a liquid phase into the rectification column immediately below the withdrawal point (at one or more recycle points). Especially in the case of gaseous withdrawal of the stream to be treated in accordance with the invention, the recycling of the liquid phase can also be effected at the height of the withdrawal point. It will be appreciated that the process according to the invention can be applied repeatedly along the rectification column. There may also be a relatively large separation between the withdrawal point and the recycle point. In the above-outlined procedure according to the invention, the removed (meth)acrylic monomers will preferably be withdrawn from the rectification column above the point at which the liquid comprising the (meth)acrylic monomers to be separated enters the rectification column. The at least one withdrawal point for the stream to be withdrawn in accordance with the invention may be disposed below and/or above this withdrawal point.

Heat required for the process according to the invention is introduced into the process according to the invention advantageously, for example, via internal and/or external heat exchangers of conventional design and/or jacket heating. Preference is given to using external circulation evaporators having natural or forced circulation. Particularly advantageous in accordance with the invention are external circulation evaporators having forced circulation. The use of a plurality of evaporators connected in series or parallel is possible in accordance with the invention.

The stream to be withdrawn from the rectification column at at least one withdrawal point in the process according to the invention may in principle be either exclusively gas phase or exclusively liquid phase or a biphasic mixture of gas and liquid phase.

The treatment of the stream withdrawn to be carried out in accordance with the invention may include highly differing treatment steps. For example, the removal of oligomerized and/or polymerized (meth)acrylic monomers described in DE-A 19501325 may form such a treatment step.

When the stream withdrawn consists exclusively of gas phase, its treatment for the purposes of the process according to the invention will include at least partial (preferably a complete) condensation, because, in accordance with the invention, at least a portion of the stream withdrawn has to be recycled into the rectification column as the liquid phase.

In general, the treatment of the stream withdrawn to be carried out in accordance with the invention will also include treatment with a source of molecular oxygen, in order to ensure that the $C_R/C_F$ ratio of $\geq 2$ is fulfilled in accordance with the invention.

Normally, the source of molecular oxygen used will be a molecular oxygen-containing gas. This source could be pure molecular oxygen or a mixture of molecular oxygen and a preferably inert gas (e.g. $N_2$). Particular preference is given to using air.

When reflux liquid is withdrawn as the stream to be withdrawn in accordance with the invention, it is advantageously fed to a delay vessel. A portion of the liquid phase present is then typically withdrawn from this delay vessel and, as required in accordance with the invention, recycled into the rectification column at at least one recycle point which is preferably disposed below the withdrawal point. Another portion of the liquid phase present in the delay vessel is likewise withdrawn, optionally (preferably not) cooled and subsequently sprayed back into the delay vessel via a spray apparatus. At the same time, air, for example, is fed to the delay vessel, from which the back-sprayed droplets of the liquid phase take up molecular oxygen and become enriched with it. The air depleted of molecular oxygen may, for example, be discharged via a venting pipe equipped with a reflux condenser.

The average delay time of the liquid phase in the delay vessel may typically be from 0.5 to 10 h. According to the invention, the delay time in the delay vessel and the air stream are preferably such that the liquid phase becomes saturated with molecular oxygen under the given boundary conditions before it is recycled into the rectification column at at least one recycle point.

In this way, $C_R/C_F$ ratios of $\geq 3$, or $\geq 5$, or $\geq 10$ or $\geq 20$, or $\geq 50$, can be achieved.

The above-described withdrawal of reflux liquid from the rectification column may be effected in various ways, for example via a chimney tray, as described in DE-A 10159615, or via a takeoff tray, as described in DE-A 4231081.

It will be appreciated that the stream to be withdrawn at at least one withdrawal point in accordance with the invention may also be a vapor. In this case, the vapor is advantageously fed to a saturator system, and at least partly condensed there by means of a directly or indirectly cooling condenser. In this case, a special takeoff and/or chimney tray may be dispensed with.

A suitable saturator is any vessel which is designed for the appropriate working pressure and the appropriate working temperature. Preference is given to using saturators which are longer than they are wide. At the bottom of the saturator, a first portion of condensate (which has been obtained by indirect and/or direct cooling) is withdrawn and nozzle-sprayed in the upper region of the saturator, optionally after preceding cooling by indirect heat exchange. According to the invention, polymerization inhibitor is advantageously added to the condensate before it is sprayed.

At the same time, air, for example, is advantageously fed in, for example in the case of the delay vessel. The indirect cooling for condensation purposes may be effected in the saturator, for example, by a tube bundle heat exchanger.

As required in accordance with the invention, a second portion of molecular oxygen-enriched condensate is recycled into the rectification column at at least one recycle point.

The temperature in the delay vessel and in the saturator is subject to no restrictions. Preference is given to selecting a temperature in the saturator which makes it possible to dispense with indirect cooling in a saturator in addition to direct cooling. The pressure in the delay vessel and in the saturator is likewise subject to no restrictions. This pressure is preferably not lower than at the withdrawal point. Very particular preference is given to operating delay vessel and saturator at atmospheric pressure.

According to the invention, the oxygenous gas is advantageously metered into the saturator in an amount of from 0.1 to 1000 m³ (STP) (preferably from 1 to 100 m³) per hour and m³ volume of the saturator. Its content of molecular oxygen is preferably from 1 to 50 mol %, more preferably from 5 to 25 mol %. In the case of vapors removed from the rectification column and having a flashpoint to DIN 51755 of $\leq 50°$ C., the molecular oxygen-containing gas preferably has a molecular oxygen content of from 4 to 10 mol %.

Normally, the partial pressure of molecular oxygen in the saturator ($P_{OS}$) is greater than the partial pressure of molecular oxygen at the recycle point ($P_{OR}$). It is advantageous when $P_{OS}/P_{OR} \geq 2$, or $\geq 10$. This is substantially also true in the case of the delay vessel.

When the rectification column is a tray column, the liquid phase treated in accordance with the invention is recycled in accordance with the invention preferably to the tray directly below the withdrawal point.

Instead of a molecular oxygen-containing gas, the source for the molecular oxygen may also be, for example, a molecular oxygen-releasing system in the saturator or in the delay vessel, provided that this releases no oxygen radicals.

In an elegant embodiment of the process according to the invention, a molecular oxygen-containing gas, for example air, flows through the rectification column from bottom to top and/or from top to bottom. In this way, even vapors which are withdrawn already contain molecular oxygen. As a consequence of the at least partial condensation occurring in the saturator, the partial pressure of molecular oxygen in the saturator rises sharply. This increased partial oxygen pressure leads to oxygen accumulation in the condensate and therefore in the liquid phase to be recycled, as desired in accordance with the invention. Uncondensable constituents (e.g. $N_2$) can in turn be conducted out of the saturator by a vent pipe equipped with a reflux condenser.

Surprisingly, the polymerization-inhibiting action of the molecular oxygen present in the liquid phase recycled into the rectification column in accordance with the invention is still detectable in a relatively large column region below the recycle point, even though the concentration of the oxygen dissolved in this liquid phase is significantly above the thermodynamic equilibrium partial pressure in the rectification column and the mass transfer processes in a rectification column are very rapid.

Preference is of course also given to operating the rectification column in the process according to the invention with polymerization inhibition. The polymerization inhibitors which are generally introduced at the top of the column may also additionally be fed to the bottom and also already have been added to the liquid comprising (meth)acrylic monomers to be separated in accordance with the invention.

Useful polymerization inhibitors here are, for example, alkylphenols, e.g. o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol, or 2,2'-methylenebis-(6-tert-butyl-4-methylphenol),
hydroxyphenols, e.g. hydroquinone, 2-methylhydroquinone, 2,5-di-tert-butylhydroquinone, pyrocatechol (1,2-dihydroxybenzene) or benzoquinone, aminophenols, e.g. para-aminophenol, nitrosophenols, e.g. para-nitrosophenol, alkoxyphenols, e.g. 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, tocopherols and also 2,3-dihydro-2,2-dimethyl-7-hydroxybenzofuran (2,2-dimethyl-7-hydroxycoumaran), N-oxyls such as 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4''-tris(2,2,6,6-tetramethylpiperidine N-oxyl) phosphite or 3-oxo-2,2,5,5-tetramethylpyrrolidine N-oxyl, aromatic amines or phenylenediamines, e.g. N,N-diphenylamine, N-nitrosodiphenylamine, N,N'-dialkylparaphenylenediamine in which the alkyl radicals may be the same or different and each independently contain from 1 to 4 carbon atoms and may be straight-chain or branched, hydroxylamines, e.g. N,N-diethylhydroxylamine, phosphorus compounds, e.g. triphenyl-phosphine, triphenyl phosphite, hypophosphorous acid or triethyl phosphite, sulfur compounds, e.g. diphenyl sulfide or phenothiazine, optionally in combination with metal salts, for example the chlorides, dithiocarbamates, sulfates, salicylates or acetates of copper, manganese, cerium, nickel or chromium. It will be appreciated that mixtures of stabilizers can also be used.

Preference is given in accordance with the invention, especially in the case of acrylic acid as the (meth)acrylic monomer, to using phenothiazine, hydroquinone monomethyl ether and/or N,N-di-sec-butyl-p-phenylenediamine. The concentration of the polymerization inhibitor system used in all liquid phases is advantageously from 100 to 5000 ppm by weight, preferably from 200 to 1000 ppm by weight, based on the weight of the liquid phase.

The way in which the stabilizer is added is likewise subject to no restriction. Preference is given to metering the stabilizer (polymerization inhibitor) as a solution or without solvents into the upper region of the rectification column. The low boiler fraction can be cooled for the purpose of condensing it in the top region, for example, using indirect heat exchangers which are known per se to those skilled in the art and are subject to no restriction, or directly, for example using a quench. Preference is given to using direct cooling. To this end, a low boiler fraction which has already been condensed is cooled by means of a suitable heat exchanger and the cooled condensate is sprayed in the vapor above the takeoff point. The condensation of the low boiler fraction may also be performed in more than one stage. When indirect cooling is used, the stabilizer is preferably sprayed from above onto the cooling unit (for example into the tubes flowed through by vapors of a tube bundle heat exchanger). When direct cooling is used, preference is given to metering the polymerization inhibitor into the quench circuit. In both cases, the rectification column is stabilized via the reflux.

For further, and/or, in extreme cases, sole, support of the procedure according to the invention, a (molecular) oxygen-containing gas, preferably air or a mixture of air and nitrogen (depleted air), is advantageously conducted through the rectification column. This oxygenous gas is preferably metered into the bottom region of the rectification unit and/or into a circulation evaporator connected to it.

It will be appreciated that the process according to the invention can also be applied coupled to all other prior art processes for suppressing polymer formation. These are in particular those of DE-A 19501325, DE-A 10238145, DE-A 10217121, DE-A 10139767 and DE-A 10223618.

The process according to the invention can be realized in a particularly efficient manner when the rectificative process relates to the removal of (meth)acrylic acid from a mixture comprising (meth)acrylic acid and an inert hydrophobic organic liquid having a higher boiling point than (meth)acrylic acid as the main constituents and also lower aldehydes as secondary constituents, as occurs, for example, in the course of the removal of (meth)acrylic acid from the reaction gas mixture of the catalytic gas phase oxidation according to the procedures described in DE-A 44 36 243, DE-C 21 36 396, EP-A 925 272 and DE-A 43 08 087. This is the case when the starting mixture comprising (meth)acrylic acid and an inert hydrophobic organic liquid having a higher boiling point than (meth)acrylic acid as the main constituents and also lower aldehydes as the secondary constituents for the process according to the invention has been obtained, for example, from the reaction gas mixtures of catalytic gas phase oxidation, as the liquid effluent of a countercurrent absorption with subsequent desorption by stripping, according to DE-C 21 36 39, EP-A 925 272 or DE-A 43 08 087 or as the liquid effluent of a countercurrent absorption with overlapping rectification according to DE-A 44 36 243. In this context, high-boiling inert hydrophobic organic liquids are those liquids whose boiling points at atmospheric pressure (1 atm) are above the boiling temperature of (meth)acrylic acid and in which the solubility (% by weight, based on the weight of the solution) of (meth)acrylic acid oligomers and/or polymers at 25° C. and 1 atm is lower than in pure (meth)acrylic acid.

These high-boiling, organic liquids are in particular those which consist of at least 70% by weight of those molecules which contain no externally acting polar group and are therefore not capable, for example, of forming hydrogen bonds. In a narrower sense, the term here includes the high-boiling organic absorption liquids recommended in DE-C 21 36 396, DE-A 43 08 087 and DE-A 44 36 243.

These are substantially liquids whose boiling point at atmospheric pressure is above 160° C. The examples include middle oil fractions from paraffin distillation, diphenyl ether, diphenyl or mixtures of the abovementioned liquids, for example a mixture of from 70 to 75% by weight of diphenyl ether and from 25 to 30% by weight of diphenyl (known as Diphyl). Another advantageous high-boiling hydrophobic organic absorption liquid is a mixture consisting of a mixture of from 70 to 75% by weight of diphenyl ether and from 25 to 30% by weight of diphenyl, and also, based on this mixture, from 0.1 to 42.5% by weight of o-dimethyl phthalate.

In the case of methacrylic acid, the catalytic oxidative preparation in the gas phase may, for example, have started from methacrolein which in turn may have been obtained by catalytic oxidation in the gas phase of tert-butanol, isobutane or isobutene or by reaction of formaldehyde with propionaldehyde according to EP-B 92 097 or EP-B 58 927. Frequently, tert-butanol, isobutane or isobutene are catalytically oxidized in the gas phase using a catalytically active composition of the general formula I $$Mo_{12}Bi_aFe_bX_c^1X_d^2X_e^3X_f^4O_n \quad (I)$$

where the variables are defined as follows:
$X^1$ is nickel and/or cobalt,
$X^2$ is thallium, an alkali metal and/or an alkaline earth metal,
$X^3$ is phosphorus, arsenic, boron, antimony, tin, cerium, lead, niobium and/or tungsten,
$X^4$ is silicon, aluminum, titanium and/or zirconium,
a is from 0.5 to 5,
b is from 0.01 to 3,
c is from 3 to 30,
d is from 0.02 to 2,
e is from 0 to 5,
f is from 0 to 10 and
n is an integer which is determined by the valency and frequency of the elements in I other than oxygen, at temperatures of from 300 to 400° C. and, apart from the special temperature program, otherwise according to the conditions of DE-A 40 23 239. The resulting methacrolein is generally used for further oxidation without intermediate purification. Apart from the special temperature program, methacrolein can be catalytically oxidized in the gas phase in accordance with the instructions of DE-A 41 32 263 at temperatures of from 200 to 350° C., or in accordance with DE-A 41 32 684 at temperatures of from 250 to 400° C.

In particular, the multimetal oxide catalysts detailed in DE-A 40 22 212 can be used.

In the case of acrylic acid, the catalytic oxidative preparation in the gas phase may, for example, have been in one stage starting from acrolein or two stages starting from propylene via acrolein. Useful multimetal oxide catalysts for the catalytic gas phase oxidation of propylene are in particular those of the general formula II $$Mo_{12}Bi_aFe_bX_c^1X_d^2X_e^3X_f^4O_n \quad (II)$$

where the variables are defined as follows:
$X^1$ is nickel and/or cobalt,
$X^2$ is thallium, an alkali metal and/or an alkaline earth metal,
$X^3$ is phosphorus, arsenic, boron, antimony, tin, cerium, lead, niobium and/or tungsten,
$X^4$ is silicon, aluminum, titanium and/or zirconium,
a is from 0.5 to 5,
b is from 0.01 to 3,
c is from 3 to 10,
d is from 0.02 to 2,
e is from 0 to 5,
f is from 0 to 10 and
n is an integer which is determined by the valency and frequency of the elements other than oxygen, and those for the catalytic gas phase oxidation of acrolein are in particular of the general formula III $$Mo_{12}V_aW_bCu_cNi_dX_e^1X_f^2X_g^3X_h^4X_i^5O_n \quad (III)$$

where the variables are defined as follows:
$X^1$ is one or more alkali metals,
$X^2$ is one or more alkaline earth metals,
$X^3$ is chromium, manganese, cerium and/or niobium,
$X^4$ is antimony and/or bismuth,
$X^5$ is silicon, aluminum, titanium and/or zirconium,
a is from 1 to 6,
b is from 0.2 to 4,
c is from 0.5 to 6,
d is from 0.2 to 6,
e is from 0 to 2,
f is from 0 to 3,
g is from 0 to 5,
h is from 0 to 40,
i is from 0 to 40 and
n is an integer which is determined by the valency and frequency of the elements other than oxygen.

The reaction gases of the first oxidation stage are typically fed to the second oxidation stage without intermediate purification. Reaction conditions which are typically employed can, for example, be taken from DE-A 44 31957 and also DE-A 44 31949.

In general, such a mixture consisting, as described above, substantially of (meth)acrylic acid and an inert hydrophobic organic liquid having a higher boiling point than (meth)acrylic acid as the main constituents and also lower aldehydes as secondary constituents contains from 5 to 25% by weight, usually from 5 to 15% by weight, of (meth)acrylic acid.

The rectificative removal of (meth)acrylic acid via a top- or sidestream of the rectification column is preferably effected at reduced pressure (advantageously at a top pressure of $\leq 500$ mbar, typically from 10 to 500 mbar, frequently from 10 to 200 mbar and preferably from 10 to 100 mbar; correspondingly, the bottom temperatures are generally from 100 to 230° C.).

EXAMPLE AND COMPARATIVE EXAMPLE a) Example

A bubble-cap tray column which had 35 equidistant bubble-cap trays and a length of 3245 mm and also an internal diameter of 80 mm was charged with an acrylic acid-containing liquid obtained as in the example of DE-A 195 01 325 which contained the following proportions:
17% by weight of acrylic acid,
0.02% by weight of water,
0.002% by weight of acrolein,
0.002% by weight of allyl acrylate,
0.01% by weight of furfural,
0.03% by weight of acetic acid,
0.2% by weight of benzaldehyde,
0.003% by weight of propionic acid,
0.03% by weight of maleic anhydride,
58% by weight of Diphyl,
17% by weight of dimethyl phthalate,
3% by weight of acryloylpropionic acid and
200 ppm by weight of phenothiazine.

The bubble-cap tray column was equipped with a jacket.

The temperature of the jacket was set to 150° C. (tray 1 to 11), 119° C. (tray 12 to 25) and 100° C. (tray 26 to 35) by means of a heat carrier oil.

The liquid to be separated was fed at a temperature of 20° C. and a rate of 3250 g/h to the 11th tray of the rectification column. The bottom temperature was 160° C. and the top temperature was 76° C. The rectification column was operated at a top pressure of 80 mbar.

The bottom liquid of the rectification column was heated to 160° C. using a forced-circulation evaporator, and the circulation rate was 500 l/h. 5000 cm³ (STP) of air were additionally metered into the evaporator.

The acrylic acid-containing liquid to be separated was separated in the rectification column into 99.6% by weight acrylic acid (pure product), a low boiler mixture (having a lower boiling point than acrylic acid) having an acrylic acid content of 96% by weight and a high boiler mixture having an acrylic acid content of 0.5% by weight. The low boiler vapor of the rectification column was condensed in a quench cooler. The quench cooler was a hollow pipe of length 700 mm and with an internal diameter of 80 mm. Already condensed vapor was nozzle-sprayed into the upper section of the hollow pipe by means of a pump. The conveying output was 1000 l/h. A heat exchanger in the pump circuit was used to set the temperature in the quench cooler to 17° C. The liquid phase in the quench cooler was inhibited with 200 ml/h of a 0.3% by weight solution of phenothiazine in pure product. 150 ml per hour of low boiler condensate were discharged and 3600 ml per hour of low boiler condensate were used as reflux. 2800 ml per hour of bottom liquid (low boiler mixture) were discharged from the bottom of the rectification column.

1400 g per hour of acrylic acid (pure product) were removed from the rectification column via a sidestream at the 25th tray. 600 g/h of this pure product were fed to a storage means. The other 800 g/h of pure product were fed at a temperature of 60° C. to a saturator via a delay vessel (capacity 2 l). The saturator was a hollow tube open to the atmosphere (length 700 mm, internal diameter 80 mm). A pump was used to nozzle-spray the pure acrylic acid product from the delay vessel repeatedly into the upper section of the hollow tube. The conveying output was 1000 l/h. The saturator was at the same time flowed through in cocurrent by 10000 cm³ (STP) of air/h. The pressure in the saturator was 1000 mbar.

The effluent from the saturator was fed to the delay vessel. 800 g/h of liquid phase were recycled from the saturator, which had a liquid holdup of 800 ml, to the 24th bubble-cap tray of the rectification column. It contained 45 ppm by weight of $O_2$. The reflux liquid fed to the 24th bubble-cap tray contained <1 ppm by weight of $O_2$.

The rectification column was operated for 40 days without impairment.

b) Comparative Example

The procedure of the example was repeated. However, the 800 g/h of pure product were conducted following removal from the 25th bubble-cap tray to the 24th bubble-cap tray avoiding the saturator (via an appropriate pipe). After a running time of 19 days, the rectification had to be terminated. In the region of trays 22 to 24, the bubble-cap trays were blocked as a consequence of polymer formation.

I claim:

1. A process for rectificatively separating liquids comprising (meth)acrylic monomers in a rectification column comprising:
    withdrawing a stream from the rectification column at at least one withdrawal point during rectification,
    treating the stream withdrawn and, after the treatment, recycling at least a portion of this stream as a liquid phase into the rectification column at at least one recycle point,
    wherein the liquid phase recycled into the rectification column has a content of molecular oxygen, $C_R$, expressed in percent by weight of the liquid phase, and a reflux liquid within the rectification column at the recycle point has a content of molecular oxygen, $C_F$, expressed in percent by weight of the reflux liquid,
    wherein a $C_R/C_F$ ratio is at least 2.

2. The process as claimed in claim 1, wherein the $C_R/C_F$ ratio is $\geq 5$.

3. The process as claimed in claim 1, wherein the $C_R/C_F$ ratio is $\geq 20$.

4. The process as claimed in claim 1, wherein the treating step is at least one treatment selected from the group consisting of removal of oligomerized and/or polymerized (meth)acrylic monomers, at least partial condensation of the stream, and introduction of a source of molecular oxygen to ensure a $C_R/C_F$ ratio of $\geq 2$.

5. The process as claimed in claim 4, wherein the treating step is removal of oligomerized and/or polymerized (meth)acrylic monomers.

6. The process as claimed in claim 4, wherein the treating step is at least partial condensation of the stream.

7. The process as claimed in claim 4, wherein the treating step is introduction of a source of molecular oxygen to ensure a $C_R/C_F$ ratio of $\geq 2$.

* * * * *